United States Patent [19]

Ahlm

[11] 4,440,817
[45] Apr. 3, 1984

[54] MEANS FOR AN ELASTIC BODY WITH PROTECTIVE LAYER

[75] Inventor: Lars Ahlm, Ulricehamn, Sweden

[73] Assignee: Timmele Laminering AB, Ulricehamn, Sweden

[21] Appl. No.: 391,688

[22] Filed: Jun. 24, 1982

[30] Foreign Application Priority Data

Jul. 3, 1981 [SE] Sweden ............................... 8104154

[51] Int. Cl.³ .................. A47C 27/15; B32B 3/04; B32B 3/06
[52] U.S. Cl. ................................ 428/71; 5/461; 5/481; 428/76; 428/286; 428/287; 428/316.6; 428/319.3; 428/319.7
[58] Field of Search ................. 5/481, 473, 471, 470, 5/461; 428/71, 76, 284, 286, 287, 316.6, 319.3, 319.7

[56] References Cited

U.S. PATENT DOCUMENTS

| | | | |
|---|---|---|---|
| 3,616,171 | 10/1971 | Hoskinson, Sr. | 5/481 |
| 3,795,722 | 3/1974 | Sassaman | 428/318.6 |
| 4,015,041 | 3/1977 | Koschatzky et al. | 428/316.6 |
| 4,088,805 | 5/1978 | Wiegand | 428/76 |
| 4,185,341 | 1/1980 | Scales | 5/461 |
| 4,357,725 | 11/1982 | Ahlm | 428/71 |
| 4,359,496 | 11/1982 | Kratel et al. | 428/76 |

FOREIGN PATENT DOCUMENTS

| | | | |
|---|---|---|---|
| 929706 | 6/1953 | United Kingdom | 428/71 |
| 1046048 | 10/1966 | United Kingdom | 5/481 |
| 2045073 | 10/1980 | United Kingdom | 5/481 |

*Primary Examiner*—William J. Van Balen
*Attorney, Agent, or Firm*—Dennison, Meserole, Pollack & Scheiner

[57] ABSTRACT

Hospital mattresses are generally made of foam plastic having predominantly open cell cores and are in the form of a parallel-epipedic block (1) which is provided with a protective layer (12 and 13) consisting of a plastic film which is easy to clean so that injurious substances and bacteria can be removed. Such mattresses have the drawback, however, that when used they produce sounds which are disturbing. These sounds are eliminated in accordance with the present invention by arranging a layer of fabric (9 and 10) between the outer surface of the foam plastic block (1) and the protective layer (12 and 13).

9 Claims, 5 Drawing Figures

MEANS FOR AN ELASTIC BODY WITH PROTECTIVE LAYER

The present invention relates to an elastic body which on its outer surface is entirely or partially provided with a protective layer. The body is generally made of a plastic which has been allowed to foam or expand. The body is thus composed of a number of cells, each enclosing a volume. Said cells are punctured to allow air to flow in and out through the cells. Puncturing of the cells is obtained by heat-treating the body. Such a body is provided entirely or partially with a film which is either placed over the body or secured through the body in one way or another. Adhesive or other known methods can be used to effect the attachment. One method is to heat the outer surface of the body so that it becomes tacky and the film applied thereon adheres to it. The purpose of the film is not to allow moisture though and it should also be of a type which will allow substances, bacteria and other particles which may adhere to the protective layer, to be easily removed with the help of a suitable cleaning agent. In certain cases treatment in an autoclave may even be advisable. Many applications are feasible for a body such as that described above which is coated with a protective layer. One application is as a bed mattress, in which case the body is generally parallel-epipedic in shape. The upper and lower surfaces and the longitudinal side surfaces of the mattress are coated with said protective layer. The transverse side surface, however, have no protective layer. This is to permit the passage of air to the cells in the mattress. The coated surfaces of such a parallel-epipedic body are generally somewhat rough and the layer applied is therefore not flat. This allows air to circulate between the upper surface and the user of the mattress. The movements of the user of such a mattress cause a creaking noise which is disturbing if the user is not alone.

The object of the present invention is to eliminate the above-mentioned disturbing sounds. This is achieved by placing a fabric layer between the body and said protective layer. The fabric may be attached both to the protective layer and to the body itself.

A suitable material for the fabric is nylon charmeuse. This may have a weight of 63 gram/m$^2$.

A suitable material for the mattress body itself is polyether. If polyether is used this should have a weight of 30 kg/m$^3$. Highly elastic cold foam consisting of cold-foamed polyether may also be used. Its weight should be 37 kg per m$^3$.

Further characteristics of the present invention are revealed in the following claim.

The present invention will be described more fully with reference to the accompanying two drawings in which the figures show a mattress in prespective at various stages of manufacture.

Figure 1:
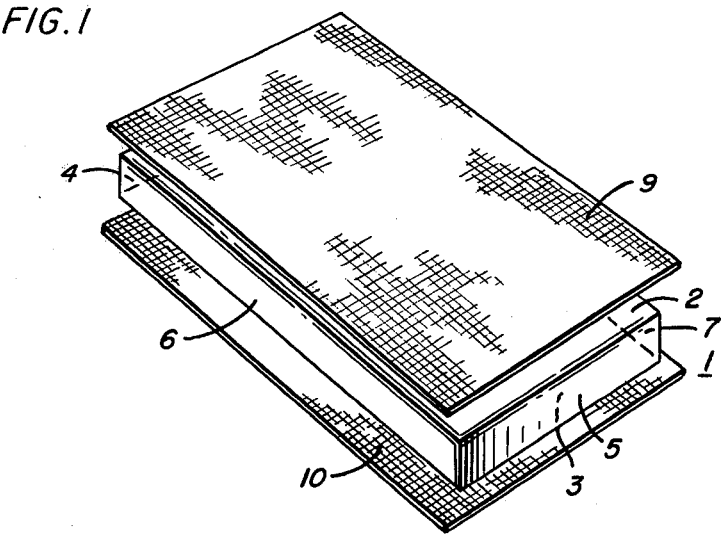
FIG. 1 shows a mattress core between fabric layers.

In the drawings 1 is a mattress consisting of a parallel-epipedic core of a plastic which has been allowed to expand to form a foam consisting of a number of cells, each enclosing a space. The cells have been penetrated by means of heat-treatment during production so that air can pass through them. A suitable material for the core is a material as above, which is also described in Table I.

TABLE I

| | |
|---|---|
| Quality | HE37 |
| Color | White |
| Standard Width | 2000 mm |
| Total Height | 860 mm +/− 3% |
| Shoulder Height | 700 mm +/− 3% |
| Bulk Density | Gr. pr. kg/M$^3$ +/− 4% 38 |
| ISO 1855/SIS 169209/DIN 53420 | Net pr. kg/m$^3$ +/− 4% 36 |
| Hardness Index (50 mm) ISO 2439/SIS 169212/DIN 53576 | 150 N +/− 4% |
| Dynamic Fatigue Height Loss ISO 3385/SIS 169212/DIN 53574 | 30 N 1.5% |
| Elongation | 220% |
| ISO 1798/SIS 169211/DIN 53571 Elongation at Break | 110 kPa |
| Deformation ISO 1856/SIS 169213/DIN 53572 | 2.0% |
| Elasticity SIS 169217 | 58% |
| Impact Strength SO 3386/DIN 53577 | 3.6 kPa +/− 6% |
| Field of Application | Cushions, Office and Dining-room Furniture, Mattresses |
| Comments | Fulfills requirements for Bulletin 117 sec. A & D STATE OF CALIFORNIA. |
| Quality | F30 |
| Color | Grey |
| Standard Width | 2000 mm |
| Total Height | 1040 mm +/− 3% |
| Shoulder Height | 880 mm +/− 3% |
| Bulk Density | Gr. pr. kg/m$^3$ +/− 5% 29 |
| ISO 1855/SIS 169209/DIN 53420 | Net pr. kg/m$^3$ +/− 5% 27 |
| Hardness Index (50 mm) ISO 2439/SIS 169212/DIN 53576 | 150 N +/= 4% |
| Dynamic Fatigue ISO 3385/SIS 169214/DIN 53574 Height Loss | 50 N 3.0% |
| Elongation | 240% |
| ISO 1798/SIS 169211/DIN 53571 Elongation at break | 100 kPa |
| Deformation ISO 1856/SIS 169213/DIN 53572 | 4.0% |
| Elasticity SIS 169217 | 46% |
| Impact Strength ISO 3386/DIN 53577 | 3.3 kPa +/− 6% |
| Field of Application | LAMINATION |
| Comments | Fulfills requirements for FMVSS 302/1972 pt. 4.3 - laminatable |

The mattress core has an upper part 2 and a lower part 3, two longitudinal sides 6 and 7 and two short sides 4 and 5. Two fabric halves are placed over the upper part 2, lower part 3 and longitudinal sides 6 and 7 so that said surfaces are completely covered by the two fabric halves. The opposite edges of the two fabric halves meet along the longitudinal sides 6 and 7. The fabric is preferably nylon charmeuse but other types of fabric may of course be used. Nylon charmeuse is described in Table II.

TABLE II

Woven Fabric   Type   Polyamide
Warp-knitted product with binding LT 1 10-34 L2 01.10
Manufactured from 44 D - Tex Polyamide, gauge 15.16/mm,
giving a weight of 63 gram/m².

Figure 2:
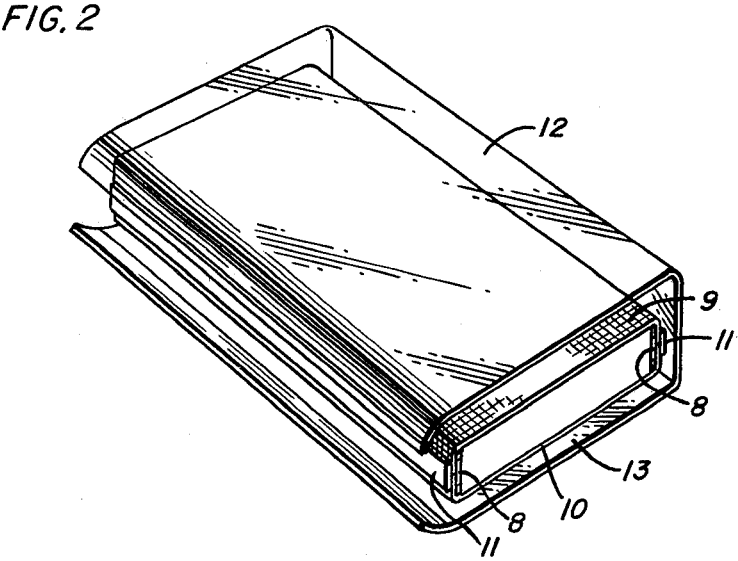
FIG. 2 shows fabric layers covering the longitudinal sides of the core and attached or about to be attached thereto by a longitudinal strip disposed between the same.
Figure 3:
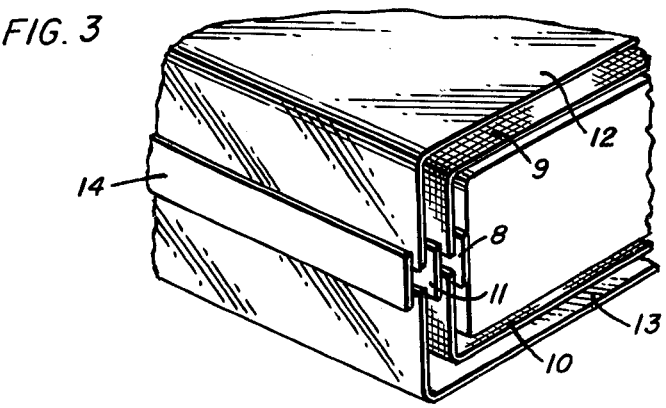
FIGS. 3 and 4 show outer plastic layers placed over the fabric layers.
Figure 4:
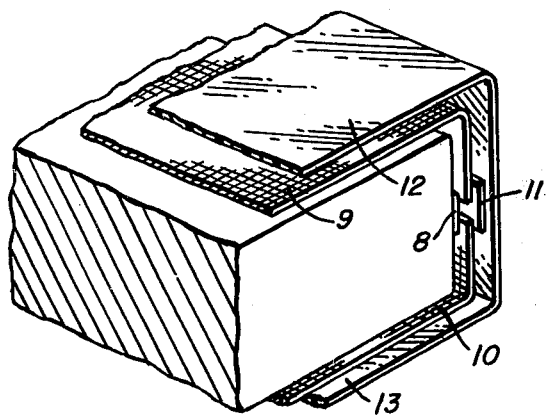
Figure 5:
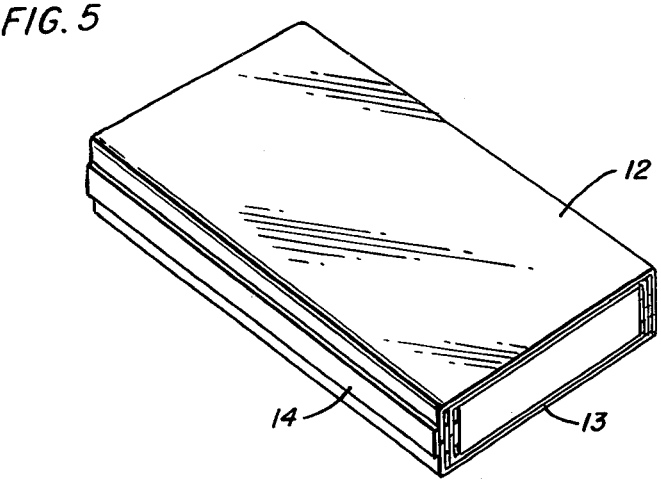
FIG. 5 show the integrated elastic body of the invention.

The fabric may be secured to the mattress core, the latter having been heated to provide a tacky surface. The pieces of fabric covering the longitudinal sides 6 and 7 may be attached thereto by strips provided with attachment means on both sides. One such strip is shown in the drawings on the longitudinal side 6. This strip is designated 8 as shown in FIG. 2. The strip on the longitudinal side 7 is identical to the strip 8. A protective layer consisting of two halves 12 and 13 is placed over the fabric layers 9 and 10. The layers 12 and 13 consist of a plastic which is non-permeable and have a surface allowing bacteria, substances and other undesirable particles to be easily removed and which will also stand treatment in an autoclave. The plastic can be secured to the fabric-covered core by heating the core, whereupon the surface becomes tacky and this tackiness can penetrate through the fabric. Should this not be so, an adhesive or a foil provided on both sides with adhesive is applied between the fabric and the protective layer. The edges of the parts 12 and 13 of the protective layer are substantially in contact with each other along the longitudinal sides 6 and 7. Said parts can be caused to adhere by heating the mattress core or by using an attachment strip coated on both sides with adhesive and arranged between the fabric layers 9 and 10 and the protective layers 12 and 13. In the drawings such an attachment strip is only visible on the longitudinal side 6 where it is designated 11. The two joints formed by the parts 12 and 13 of the protective layer on the longitudinal sides 6 and 7 are covered by a covering strip, denoted 14 on the longitudinal side 6 as shown in FIG. 3. A suitable plastic for the protective layer is highly elastic polymer film. The plastic is described in Table III.

TABLE III

| | | | TF-310 312.330-800 | | TF-410 | |
| | | Physical properties | | | | |
| | Standard | | Polyester | | Polyether | |
| Test | ASTM | | 1 Mil | 3–5 Mil | 1 Mil | 3–5 Mil |
| --- | --- | --- | --- | --- | --- | --- |
| Specific Gravity | D-792 | | 1.22 | 1.22 | 1.14 | 1.14 |
| Hardness Shore, A | D-2240 | | 93 (50D) | 93 (50D) | 82 | 82 |
| Stress-Strain | D-883 | | | | | |
| Ultimate Strength psi (MPA) | | MD* | 9000 (62.1) | 8500 (58.7) | 6000 (41.4) | 6500 (44.8) |
| | | TD* | 5000 (34.5) | 8100 (55.9) | 3000 (20.7) | 5200 (35.9) |
| 100% Modulus, psi (MPA) | | MD | 3000 (20.7) | 1600 (11.4) | 1700 (11.7) | 800 (5.5) |
| | | TD | 1100 (7.6) | 1600 (11.0) | 530 (3.7) | 660 (4.6) |
| 300% Modulus, psi (MPA) | | MD | | 4900 (33.8) | | 1500 (10.3) |
| | | TD | | 4800 (33.1) | | 1100 (7.6) |
| Elongation at Break, % | | MD | 200 | 410 | 350 | 570 |
| | | TD | 400 | 410 | 650 | 630 |
| Tear Initiation, Graves, lb/in (kg/cm) | D-1004 | MD | 250 (44.8) | 500 (107.4) | 250 (44.8) | 430 (77.0) |
| | | TD | 500 (89.5) | 560 (100.2) | 380 (68.0) | 420 (75.2) |
| Tear Propagation, lb/in (kg/cm) | D-1938 | MD | 250 (46.5) | 500 (89.5) | 260 (46.5) | 212 (37.9) |
| | | TD | 400 (71.6) | 560 (100.2) | 250 (44.8) | 272 (48.7) |
| Moisture Vapor Transmission, gm/24 hr/100 sq. in. | E-95-E | | 46 | 23 | 76 | 43 |
| Abrasion Resistance, Taber CS-17 5000 Cycles; 1,000 gm load; 75 mil sample; mg lost Taber | | | 3 | 3 | 8 (1000 cycles) | |
| Impact Strength lb/in (kg/cm) | D-1709 | | 400 (71.7) | 400 (71.7) | 390 (69.9) | |
| Permeation Properties | | | | | | |
| Gas transmission rate, cc/24 hr/100 sq. in. | D-1434 | | | | | |
| Oxygen | | | 75 | 72 | 1000 | 542 |
| Nitrogen | | | 45 | 18 | 450 | 151 |
| Carbon Dioxide | | | 450 | 729 | 4300 | 6902 |
| Air | | | 55 | 28 | NA | 214 |
| Helium | | | NA | 349 | NA | 1188 |
| MVT gm/mil/24 hr/100 sq. in. | E-96-E | | 8.6 | | 1.86 | |
| Thermal Properties (075" sample) Solenoid Brittle pt, °F. (°C.) | D-746 | | −80 (−62) | | −100 (−73) | |
| Masland Cold Crack, °F. (°C.) | D-1790 | | −100 (−73) | | −100 (−73) | |
| Gehman Stiffness Modulus, psi (mpa) | D-1053 | | | | | |
| @ Room Temp. | | | 1700 (11.7) | | 570 (4.1) | |
| @ 32° F. (0° C.) | | | 2800 (19.3) | | 750 (5.2) | |
| @ 0° F. (−17.8° C.) | | | 17500 (120.7) | | 1000 (6.9) | |
| @ −40° F. (−40° C.) | | | — | | 5900 (40.7) | |
| Heat Seal Range | | | | | | |
| °F. | | | 350–400 | | 350–400 | |
| °C. | | | 176–204 | | 176–204 | |

NA - Data not available
*MD — Machine Direction, TD — Transverse Direction

Immersion data
28 days @ 23° C. (73° F.) 5 mil film

| | Ultimate Tensile psi | | Tensile Change (%) | | Ultimate Elong. (%) | | Elong. Change (%) | | Volume Change (%) | | Weight Change (%) | |
| --- | --- | --- | --- | --- | --- | --- | --- | --- | --- | --- | --- | --- |
| Test- Base Material- | Ester | Ether | Ester | Ether | Ester | Ether | Ester | Ether | Ester | Ether | Ester | Ether |

TABLE III-continued

| | | | | | | | | | | | |
|---|---|---|---|---|---|---|---|---|---|---|---|
| Original | 8500 | 5400 | — | — | 410 | 570 | — | — | — | — | — | — |
| ASTM Fuel A | 7900 | 6500 | −71 | 0 | 405 | 610 | −1.2 | +7.0 | +4.7 | −0.1 | +2.7 | |
| ASTM Fuel B | 6200 | 4300 | −27 | −34 | 460 | 150 | +12 | +7.0 | +8.7 | +18 | +8.3 | +16 |
| ASTM Fuel C | 7000 | 3800 | −17 | −42 | 510 | 590 | +24 | +3.5 | +10 | +34 | +9 | +30 |
| ASTM Oil Type 1 | 8100 | NA | −6 | NA | 380 | NA | −7 | NA | +13 | NA | +1.5 | — |
| ASTM Oil Type 2 | 6700 | 6850 | −21 | +4.6 | 390 | 590 | −4.9 | +3.5 | +5.0 | +4 | +4.5 | |
| ASTM Oil Type 3 | 7400 | 3900 | −12 | −40 | 430 | 540 | +4.9 | −5.3 | +3.2 | | +24 | +10 |
| Perchcloroehylene | 6500 | 3000 | −24 | −54 | 420 | 510 | +15 | −10.5 | +20 | +73 | +22 | +94 |
| Trichloroethylene | 4800 | 2000 | −44 | −69 | 460 | 420 | +12 | −26 | +54 | +242 | +51 | +270 |
| Benzene | 5500 | 3300 | −35 | −29 | 500 | 670 | +22 | +17 | +38 | +108 | +30 | +95 |
| MEK | 3600 | * | −58 | 550 | * | +34 | * | * | +30 | * | +27 | |
| Isopropyl Alcohol | 5300 | 300 | −38 | −95 | 510 | 670 | +24 | +17 | +11 | +34 | +9 | +26 |
| Saturated NaCl | 7500 | 5300 | −12 | −18 | 410 | 560 | 0 | −1.8 | −0.7 | NA | −0.6 | — |
| Ethylene Glycol | 6800 | 5650 | −20 | −13 | 420 | 650 | +2.4 | +14 | +4 | +4 | +4 | +4 |
| 20% NaOH | * | 4800 | * | −26 | * | 620 | * | +8.8 | −27 | +5 | −27 | +6 |
| 20% H$_2$SO$_4$ | 6600 | 2500 | −22 | −26 | 465 | 450 | 13.4 | −2.1 | +0.7 | +1.4 | +1.2 | +2.1 |
| 50% Formic Acid | * | 2600 | * | −60 | * | 680 | * | +19 | * | −17 | — | +6 |
| Synthetic Perspiration | 7300 | 5200 | −14 | −20 | 400 | 585 | +2.4 | +2.6 | +2.3 | * | — | +1.3 |
| H$_2$O @ 70° C. (158° F.) | 3500 | 5200 | −59 | −20 | 450 | 680 | +9.8 | +19 | +0.4 | NA | +1.6 | NA |
| 95% RH @ 70° C. (150° F.) | 1400 | 3700 | +83 | +43 | 170 | 620 | −59 | +8.7 | — | — | — | — |

*sample dissolved
NA - Data not available

Physical Properties
Flame Retardant
Polyether Base Material

| | Typical Properties | ASTM Test Procedure |
|---|---|---|
| UL Vertical 94 Flame Test | V O | — |
| Tensile, psi | 4700 | D412 |
| 100% Modulus, psi | 850 | — |
| 300% Modulus, psi | 1350 | — |
| Elongation, % | 570 | — |
| Graves Tear, pli | 370 | D624 |
| Crescent Tear, pli | 460 | D624 |
| Hardness, A-C-D | 87-58-41 | D2240 |
| Taber Abrasion, mgm loss, CS-17 wheel, 1000 gm, 1000 cycles | 6.2 | — |
| Vicat B, °C. | 94 | D1525 |
| Brittleness Temp | −70° C. | D746 |
| Gehman RT Modulus | 1250 | D1053 |
| T$_2$ | −15° C. | — |
| T$_3$ | −31° C. | — |
| T$_{30}$ | −37° C. | — |
| T$_{60}$ | −51° C. | — |
| T$_{100}$ | — | — |
| Freeze Point | −51° C. | — |
| Compression Set, 22 hours, RT | 23% | D395 |
| Compression Set, 22 hours, 70° C. | 66% | — |
| Specific Gravity | 1.226 | — |

The mattress core described above is thus surrounded by a fabric layer and a protective layer on four sides, two sides remaining uncovered, i.e. the short sides 4 and 5. Said sides are left uncovered in order to allow air to flow freely in and out of the mattress to retain its elasticity.

One application for the invention has been described above, that of a mattress. However, it should be obvious that the invention can also be used for cushions, pillows, car-seats, back-rests in furniture and for other applications where it is desired to avoid the sound effects mentioned above.

I claim:

1. An integrated elastic body comprising a predominantly open cell foam plastic core, an inner noise suppressing fabric layer overlying said core and stabilized relative thereto, and an outer non-permeable plastic protective layer overlying said inner layer and unitarily bonded to said inner layer and said core, wherein said body further comprises attachment strips interposed between said core, said inner fabric layer and said outer protective layer, and a covering strip disposed over at least a portion of said outer protective layer.

2. An integrated elastic body according to claim 1, wherein said inner fabric layer is secured to at least a portion of said core by the application of heat sufficient to plasticize a portion of said core surface and thereby adhere said fabric layer to said core.

3. An integrated elastic body according to claim 1, wherein said outer protective plastic layer is secured to at least a portion of said fabric covered core by the application of heat sufficient to plasticize a portion of said core surface wherein the plasticized portion of said core surface penetrates through said inner fabric layer and contacts said outer protective layer thereby adhering said outer layer to said inner fabric layer and said core.

4. An integrated elastic body according to claim 1, wherein the inner noise suppressing fabric layer is attached to at least a portion of said core by an attachment strip coated on both sides with an adhesive and interposed between said core and said inner fabric layer.

5. An integrated elastic body according to claim 1, wherein said outer protective layer is attached to at least a portion of said inner fabric layer by an attachment strip coated on both sides with an adhesive and interposed between said outer layer and said inner fabric layer.

6. An integrated elastic body according to claim 1 wherein at least two sides of said core remain uncovered in order to allow air to flow freely through said core.

7. An integrated elastic body according to claim 1, wherein said core material is polyether.

8. An integrated elastic body according to claim 1, wherein said inner fabric layer is nylon charmeuse.

9. An integrated elastic body according to claim 1, wherein said outer layer is an elastic polymer film.

* * * * *